United States Patent
Dams et al.

(10) Patent No.: US 6,512,138 B1
(45) Date of Patent: *Jan. 28, 2003

(54) PREPARATION OF (METH)ACRYLATES

(75) Inventors: Albrecht Dams, Wachenheim (DE); Heinrich Aichinger, Mannheim (DE); Holger Herbst, Frankenthal (DE); Gerhard Nestler, Ludwigshafen (DE); Jürgen Schröder, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/567,983

(22) Filed: May 10, 2000

(30) Foreign Application Priority Data

May 18, 1999 (DE) ......................... 199 22 722

(51) Int. Cl.$^7$ ..................... C07C 69/52; C07C 67/30; C07C 67/03
(52) U.S. Cl. ............... 560/205; 560/212; 560/218
(58) Field of Search ............... 560/212, 218, 560/205

(56) References Cited

U.S. PATENT DOCUMENTS

| | | | | |
|---|---|---|---|---|
| 3,227,746 A | * | 1/1966 | Knorr et al. ............. | 560/212 |
| 3,868,410 A | * | 2/1975 | Horlenko et al. ......... | 560/205 |
| 3,882,167 A | * | 5/1975 | Lohmar et al. .......... | 560/205 |
| 4,250,328 A | * | 2/1981 | Fujita et al. ............. | 560/205 |
| 4,329,492 A | * | 5/1982 | Andoh et al. ............ | 560/205 |
| 4,435,594 A | * | 3/1984 | Matsumura et al. ...... | 560/205 |
| 4,733,004 A | * | 3/1988 | Pascoe ................... | 560/205 |
| 5,767,306 A | | 6/1998 | Aichinger et al. | |
| 5,910,603 A | | 6/1999 | Aichinger et al. | |

FOREIGN PATENT DOCUMENTS

| | | |
|---|---|---|
| DE | 23 39 529 | 2/1975 |
| DE | 195 47 485 | 5/1996 |
| DE | 195 47 459 | 7/1996 |
| EP | 0 765 860 | 4/1997 |
| EP | 0 767 163 | 4/1997 |
| EP | 0 779 268 | 6/1997 |
| EP | 0779268 A1 * | 6/1997 |
| JP | 08 183 756 | 7/1996 |

OTHER PUBLICATIONS

Takashi Ohara, et al., Ullmanns Encycl. Ind. Chem., vol. A1, pp. 161–176, "Acrylic Acid and Derivatives", 5$^{th}$ Edition.

* cited by examiner

*Primary Examiner*—Alan L. Rotman
*Assistant Examiner*—Taylor V. Oh
(74) *Attorney, Agent, or Firm*—Oblon, Spivak, McClelland, Maier & Neustadt, P.C.

(57) ABSTRACT

The process for the esterification of (meth)acrylic acid with an alkanol in the presence of an esterification catalyst, in which unconverted starting compounds and the (meth) acrylate to be formed are separated off by distillation and an oxyester-containing bottom product is formed and is separated off, and (a) in the bottom product separated off, the oxyesters present are cleaved, if required after the addition of (meth)acrylic acid and/or oligomeric (meth)acrylic acid, directly in the presence of acid catalysts differing from (meth)acrylic acid and/or oligomeric (meth) acrylic acid, and the cleavage products are removed, a cleavage residue remaining, or (b) the oxyesters are first removed by distillation from the cleavage product separated off, a distillation residue remaining, and the oxyesters removed are cleaved, if required after addition of (meth)acrylic acid and/or oligomeric (meth)acrylic acid, in the presence of acid catalysts differing from (meth)acrylic acid and/or oligomeric (meth)acrylic acid, and the cleavage products are removed, a cleavage residue remaining, is carried out in such a way that the cleavage residue obtained in step (a) or the cleavage residue obtained in step (b) is hydrolytically cleaved together with the resulting distillation residue in the presence of water and acids or bases.

15 Claims, No Drawings

PREPARATION OF (METH)ACRYLATES

The present invention relates to a process for the preparation of (meth)acrylates, in which (meth)acrylic acid is esterified with alkanols in the presence of esterification catalysts. After the esterification, unconverted starting compounds and the (meth)acrylate to be formed are separated off by distillation, and an oxyester-containing bottom product is obtained. In addition to the oxyesters, oligomeric (meth)acrylic acid and oligomeric or polymeric (meth)acrylates are also formed. These compounds and their formation are first explained below.

Owing to their activated C=C double bond, alkyl esters of (meth)acrylic acid are important starting compounds for the preparation of polymers to be produced by free radical polymerization and used, for example, as adhesives.

Usually, the preparation of the esters is carried out by esterification of the. (meth)acrylic acid with alkanols at elevated temperatures in the liquid phase with or without a solvent and in the presence of, as a catalyst, acids other than (meth)acrylic acid, and subsequent isolation by distillation.

The disadvantage of this process is that, on the one hand, the formation of polymeric (meth)acrylates cannot be completely prevented in spite of the use of polymerization inhibitors and, on the other hand under the abovementioned esterification conditions, unconverted starting alkanols undergo an addition reaction at the double bond of already formed alkyl (meth)acrylate with formation of a compound of the formula I shown below and unconverted (meth)acrylic acid undergoes an addition reaction at said double bond with formation of a compound of the formula II, as secondary reaction (Michael addition).

Successive multiple addition is also possible. Furthermore, mixed types can occur. These adducts (alkoxyesters and acyloxyesters) are referred to as oxyesters for short:

RO(—CH$_2$—CHR'—CO$_2$)$_x$—R (I)

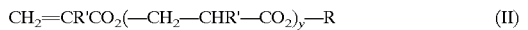
CH$_2$=CR'CO$_2$(—CH$_2$—CHR'—CO$_2$)$_y$—R (II)

where x and y are each an integer from 1 to 5,
R is alkyl and
R' is H or CH$_3$.

The formation of oxyesters is described, for example, in DE-A 23 39 529. The formation of oxyesters takes place essentially independently of the specific esterification conditions. Oxyester formation in the preparation of acrylates is of very particular importance.

The term polymeric (meth)acrylates means the polymeric products formed by free radical polymerization of (meth)acrylates. In contrast to the Michael adducts, these polymers cannot be cleaved back into the starting monomers under conventional reaction conditions. They form when the (meth)acrylates are subjected to thermal stress, for example in the synthesis or working-up of the esterification mixture by distillation or in the purification by distillation.

The term (meth)acrylic acid refers to acrylic or methacrylic acid.

The term oligomeric (meth)acrylic acid means the Michael adducts of (meth)acrylic acid with itself and with the resulting secondary products. Such Michael adducts can be characterized by the formula (III)

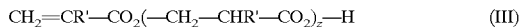
CH$_2$=CR'—CO$_2$(—CH$_2$—CHR'—CO$_2$)$_z$—H (III)

where z is an integer from 1 to 5 and
R' is H or CH$_3$, and should be distinguished here from (monomeric) (meth)acrylic acid and from (meth)acrylic acid polymers (which are obtainable by free radical polymerization of (meth)acrylic acid). What is important is that the Michael addition of (meth)acrylic acid with itself and with the resulting secondary products is reversible.

Oligomeric (meth)acrylic acid is obtained in the bottom product, for example in the distillative treatment of (for example crude) (meth)acrylic acid (the term "crude" indicates a small fraction of in particular aldehydic impurities which are still present).

Any esterification mixture is usually worked up by separating off unconverted starting compounds and the desired ester from the reaction mixture by distillation, the acid catalyst used for the esterification and unconverted (meth)acrylic acid being separated off previously, if required, by extraction by means of water and/or aqueous alkali (cf. for example Ullmann's Encyclopedia of Industrial Chemistry, Vol. A1, 5th Ed., VCH, page 167 et seq.). The bottom product remaining in such a working-up by distillation contains the oxyesters and the polymeric (meth)acrylates, which result in a considerably lower yield.

Attempts were therefore made to use a wide range of procedures to reduce the losses of desired products which are due to the occurrence of these byproducts, especially the Michael adducts.

DE-A-195 47 459 and DE-A-195 47 485 describe processes for the esterification of (meth)acrylic acid with an alkanol, in which, after the esterification reaction, the resulting (meth)acrylate and unconverted starting compounds are distilled off from the reaction mixture and an oxyester-containing bottom product forms. Either (meth)acrylic acid or oligomeric (meth)acrylic acid is added directly to the bottom product and the oxyesters contained in the bottom product are then cleaved by the action of elevated temperatures in the presence of acid catalysts which differ from (meth)acrylic acid or oligomeric (meth)acrylic acid, or the oxyesters are first separated from the bottom product by distillation and the distillate is treated as described above. The cleavage products obtained are recycled directly to the esterification. The cleavage residue remaining after the cleavage and removal of the cleavage products is not worked up further.

EP-A-0 765 860 describes a process for the esterification of (meth)acrylic acid with an alkanol, in which, after the reaction, resulting (meth)acrylates and unconverted starting compounds are separated from an oxyester-containing bottom product. The oxyesters contained in the bottom product separated off are isolated by distillation and the resulting distillate is cleaved at elevated temperatures in the presence of acids. No working up of the cleavage residue is described.

EP-A-0 767 163 describes a further process for the esterification of (meth)acrylic acid with an alkanol. After removal of resulting (meth)acrylates and unconverted starting compounds, the bottom product is separated off and is heated to 150 to 200° C. in the presence of acid, the pressure being set so that the cleavage products formed during cleavage of the oxyesters contained in the bottom product immediately evaporate off. No further treatment of the cleavage residue is described.

JP-A H8 183 756 describes the acid-catalyzed degradation of Michael adducts in the presence of water. However, the conversion is only about 60%.

EP-A-0 779 268 describes a process for the preparation of alkyl acrylates, in which the high-boiling residues (oxyesters) are hydrolytically cleaved, the alkanol formed is separated off by distillation and the hydrolysis residue is subjected to a cleavage reaction.

The process has the disadvantage that the recovery rate is unsatisfactory and that the alkyl acrylate component contained in the oxyester is hydrolytically cleaved into alkanol and acrylic acid and is not recovered as such.

It is an object of the present invention to provide a process for the esterification of (meth)acrylic acid with an alkanol, in which, compared with the above processes, the amount of byproducts is further reduced and more products which can be recycled to the esterification or removed as desired ester are obtained from the remaining residues.

We have found that this object is achieved, according to the invention, by a process for the esterification of (meth)acrylic acid with an alkanol in the presence of an esterification catalyst, in which unconverted starting compounds and the (meth)acrylate to be formed are separated off by distillation and an oxyester-containing bottom product is formed and is separated off, and (a) in the bottom product separated off, the oxyesters present are cleaved, if required after the addition of (meth)acrylic acid and/or oligomeric (meth)acrylic acid, directly in the presence of acid catalysts differing from (meth)acrylic acid and/or oligomeric (meth)acrylic acid, and the cleavage products are removed, a cleavage residue remaining, or (b) the oxyesters are first removed by distillation from the cleavage product separated off, a distillation residue remaining, and the oxyesters removed are cleaved, if required after addition of (meth)acrylic acid and/or oligomeric (meth)acrylic acid, in the presence of acid catalysts differing from (meth)acrylic acid and/or oligomeric (meth)acrylic acid, and the cleavage products are removed, a cleavage residue remaining, wherein the cleavage residue obtained in step (a) or the cleavage residue obtained in step (b) is hydrolytically cleaved together with the resulting distillation residue in the presence of water and acids or bases.

The advantage of the novel process is that the byproducts, oxyesters and polymeric (meth)acrylates obtained in the preparation of (meth)acrylates are converted, depending on their chemical nature, selectively into desired products which can be recycled directly to the esterification. High yields, high cleavage rates, high-quality cleavage products (esters) and small and readily handled amounts of residue are obtained. Esters and alkanols or esters and (meth)acrylic acid are obtained by selective cleavage of the oxyesters. Alkanols are obtained by the hydrolytic cleavage of the polymeric residues.

On the other hand, hydrolytic cleavage of the bottom product of the esterification, which product contains the oxyesters and the polymeric (meth)acrylates, gives mainly alkanol and (meth)acrylic acid or salts thereof, the isolation of the (meth)acrylic acid being extremely inconvenient.

The novel process has the following steps:

First, an esterification mixture is prepared in a known manner by esterification of (meth)acrylic acid with an alkanol in the presence of an esterification catalyst.

In the esterification, the alkanol used is preferably a $C_{1-12}$-alkanol, particularly preferably $C_{4-10}$-alkanol. Preferably, it is methanol, ethanol, n-butanol or 2-ethylhexanol, in particular n-butanol or 2-ethylhexanol.

Typical conditions under which the esterification can take place are, for example:

Alcohol:(meth)acrylic acid ratio: 1:0.7–1.2 (molar)

Catalyst: sulfuric acid or sulfonic acid (e.g. p-toluenesulfonic acid)

Amount of catalyst: 0.1–10% by weight (preferably 0.5–5% by weight, based on starting materials)

Stabilization: 200–2000 ppm of phenothiazine (based on the weight of the starting materials)

Reaction temperature: 80–160° C., preferably 90–130° C.

Reaction time: 1–10, preferably 1–6, hours.

If required, an entraining agent (e.g. cyclohexane or toluene) is used for removing the water of esterification. The esterification can be carried out under atmospheric, super-atmospheric or reduced pressure and either continuously or batchwise.

After the esterification, the esterification catalyst is removed from the reaction mixture, for example by treating the reaction mixture with water. The (meth)acrylate formed and the unconverted starting compounds are separated off by distillation.

In the acid-catalyzed esterification of acrylic acid with alkanols, the bottom product resulting after removal of the acidic esterification catalyst, of the unconverted starting materials and of the acrylate has, as a rule, the following composition:

1–20% by weight of acrylate

50–80% by weight of alkoxypropionates (cf. formula I)

3–30% by weight of acryloyloxypropionates (cf. formula II)

5–20% by weight of polymers of the acrylates

Remainder: mainly inhibitors

The oxyesters contained in the bottom product are then cleaved either directly in the bottom product or after removal from the bottom product by distillation. The direct acid-catalyzed oxyester cleavage in the bottom product is described, for example, in EP-A-0 767 163. The removal of the oxyesters by distillation and subsequent cleavage is described, for example, in EP-A-0 765 860. The cleavage of the oxyesters in the presence of monomeric and/or oligomeric (meth)acrylic acid is described, for example, in DE-A-195 47 485 and DE-A-195 47 459.

Typical conditions for carrying out the process for the cleavage of the oxyesters obtained in the bottom product during the esterification or separated off from the bottom product are the following:

Catalyst: At least one acid from the group consisting of the mineral acids, such as sulfuric acid and phosphoric acid, and organic, if required aqueous, acids differing from oligomeric (meth)acrylic acid, such as alkane- or arylsulfonic acids, e.g. dodecanesulfonic acid or p-toluenesulfonic acid Amount of catalyst: 1–20, preferably 5–15, % by weight, based on the amount of the bottom product or on the amount of the oxyester distillate separated off from the bottom product Amount of monomeric and/or oligomeric (meth)acrylic acid: 5–50, preferably 10–40, % by weight, based on the amount of bottom product or on the amount of oxyester distillate separated off from the bottom product Temperature: 150–250° C., preferably 180–230° C.

Pressure: Preferably atmospheric or reduced pressure (<1 atm), so that the cleavage products evaporate off immediately Stripping gas, if required: Amount: 1–100 l/h×l (preferably oxygen-containing gas)

Reaction time: 1–10 hours

For the cleavage of the oxyesters obtained in the bottom product during the esterification or of the oxyester distillate separated off from the bottom product of the esterification, a simple heatable stirred reactor with double-jacket heating or heating coils or a forced-circulation evaporator, for example a falling-film evaporator or flat evaporator, coupled with a dwell tank, may be used. For better separation of the cleavage products from the bottom product or oxyester distillate, a rectification apparatus, for example a packed column or tray column, mounted on the cleavage apparatus may be expedient. This rectification apparatus is stabilized as a rule with polymerization inhibitors (e.g. phenothiazine, hydroquinone monomethyl ether, etc.).

The reaction takes place, for example, by a procedure in which the product to be cleaved is removed continuously from the distillative working-up of the esterification mixture and is fed, with the cleavage catalyst and any monomeric and/or oligomeric (meth)acrylic acid, to the cleavage reactor. However, the reaction can also be carried out batchwise. A semicontinuous reaction procedure, in which the product to be cleaved and any monomeric and/or oligomeric (meth)acrylic acid are fed continuously to the cleavage reactor, which contains the cleavage catalyst, and the bottom product is removed batchwise from the cleavage reactor only after the end of the cleavage, is also possible. The cleavage products are separated off continuously by distillation and expediently recycled to the esterification.

It has proven advantageous if a stripping gas, which preferably contains molecular oxygen, is passed through the product to be cleaved, as an entraining agent for the cleavage products. An expediently used stripping gas is air or a mixture of air with inert gas (e.g. nitrogen).

In the separation of the oxyesters from the bottom product by distillation, the distillation conditions depend on the type of alkanol component used in the esterification. As a rule, a temperature of from 100 to 300° C. and a pressure from 1 to 50 mbar are envisaged. Any conventional distillation apparatus is suitable for the distillation process. Since only a simple separation problem must be solved, as a rule a simple splashguard is sufficient, i.e. a column is not usually required.

After removal of the cleavage products formed during the cleavage, a cleavage residue remains. If the oxyesters are first separated by distillation from the bottom product formed in the esterification, a distillation residue also remains. These, if necessary, combined residues are then hydrolytically cleaved in the presence of water and acids or bases.

Preferred hydrolysis conditions are as follows:

The hydrolysis can be carried out under atmospheric pressure, i.e. at ambient pressure, reduced pressure or superatmospheric pressure. The hydrolysis of the residues can be carried out in an apparatus analogous to that used for the cleavage. It can be carried out either continuously or batchwise. It is preferably carried out batchwise in a stirred reactor with double-jacket heating.

If the hydrolysis is carried out under acid catalysis, as a rule the strong acid contained in the cleavage residue is sufficient. However, the addition of further acids, for example mineral acids, such as sulfuric acid or; phosphoric acid, p-toluenesulfonic acid or other organic acids, as described above, may be expedient for increasing the reaction rate (1–20% by weight).

If the hydrolysis is catalyzed by bases, preferably alkalis and alkaline earths, the amount of the acidic cleavage catalyst present should be taken into account. As a rule, 10–50% by weight, based on the residues, of base are sufficient.

The amount of water generally to be added at the beginning is 20–200%, preferably 50–150%, based on the organic phase, regardless of the type of hydrolysis catalyst.

The hydrolysis is carried out, for example, by a procedure in which the residues, the catalyst and the water are initially taken in a stirred reactor and are heated to the boil, the hydrolysis products formed during cleavage and some of the water being distilled off. The resulting distillate separates into an aqueous phase, which, after phase separation, is recycled to the hydrolysis, and an organic phase, which mainly comprises the corresponding alkanol. The organic phase is preferably recycled directly to the esterification or to the esterification reactor.

In the hydrolytic cleavage, a stripping gas, as described above, can be passed through the cleavage residue and any distillation residue.

The Examples which follow illustrate the invention.

EXAMPLE 1

(A) Distillation of the Oxyesters

A distillation apparatus comprising a round-bottomed flask (61), an attached column (30 cm×2.8 cm; 5 mm Raschig rings) and a condenser was filled with 4 kg of a bottom liquid obtained in the preparation of butyl acrylate, no longer containing any acidic esterification catalyst and having the following composition:

7.4% by weight of butyl acrylate 64.5% by weight of butoxyester I (R=$C_4H_9$)

19.2% by weight of acyloxyester II (R=$C_4H_9$)

Remainder: mainly polymers and phenothiazine (polymerization inhibitor)

The distillation was carried out at 30 mbar up to 150° C. The resulting distillate (90% of the amount used) contained the following, according to gas chromatographic analysis:

8.5% by weight of butyl acrylate 68.3% by weight of butoxyester I (R=$C_4H_9$)

20.0% by weight of acyloxyester II (R=$C_4H_9$)

Stabilization of the column with phenothiazine or another conventional stabilization was not necessary. The resulting bottom product of the distillation was easy to handle (pumpable) at 25° C. and contained no solids.

(B) Cleavage of the Oxyesters

A circulation reactor (volume 1 l) consisting of glass and heated with a heating cartridge was filled with 500 g of the oxyester distillate from (A), 40 g of p-toluenesulfonic acid and 150 g of acrylic acid (stabilized with 300 ppm of phenothiazine) also being added.

The cleavage temperature was 195° C. and the operating pressure was 1 atm.

The oxyester distillate from (A) which was to be cleaved and the corresponding added acrylic acid (30% by weight) were fed continuously to the cleavage reactor the level being used for controlling the feed. The cleavage products were condensed at the top of the column (50 cm×2.8 cm, empty) attached to the reactor.

Per hour, 100 g of oxyester distillate and 30 g of stabilized acrylic acid were fed to the cleavage and 125.5 g of condensate were obtained. According to gas chromatographic analysis, the condensate contained:

71.8% by weight of butyl acrylate 5.1% by weight of butanol 18.2% by weight of acrylic acid 0.5% by weight of dibutyl ether 1.8% by weight of butenes Conversion: about 96.5%, based on oxyester This corresponded to about 810 g of butyl acrylate and about 58 g of butanol per 1000 g of bottom product of the esterification.

(C) Hydrolysis of the Cleavage Residue and Bottom Product of the Distillation

In a stirred reactor (2 l) consisting of glass and having an attached column (60cm×2.8 cm; 5 mm Raschig rings) and condenser, a mixture of 400 g of bottom product from the distillation from (A) and 195 g of cleavage residue (B) and 600 g of 10% strength sulfuric acid was heated to the boil while stirring, and water and hydrolysis products were distilled off continuously. The aqueous phase of the condensate was recycled to the reactor (reflux) and the organic phase was isolated (214 g). According to gas chromatographic analysis, said organic phase contained 28.6% of butyl acrylate and 52.6% of butanol. Altogether (cleavage+hydrolysis), about 825 g of butyl acrylate and about 86 g of butanol were obtained from 1000 g of bottom product of the esterification.

EXAMPLE 2 (Comparative Example)

In the apparatus described under Example 1 (C), 600 g of the bottom liquid used under Example 1 (A) were hydrolyzed in the presence of 20 g of sulfuric acid analogously to (C). 415 g of organic phase were obtained, which, according to gas chromatographic analysis, contained 7.7% of butyl acrylate and 75.7% of butanol. Accordingly, it was possible to recover only about 53 g of butyl acrylate and about 523 g of butanol per 1000 g of bottom product of the esterification.

EXAMPLE 3

(A) Cleavage of the Esterification Residue

A circulation reactor (volume: 1 l) consisting of glass and heated with a heating cartridge was filled with 500 g of an esterification residue freed from the acidic esterification catalyst and obtained from the n-butyl acrylate preparation, 150 g of acrylic acid (stabilized with 300 ppm of phenothiazine) and 50 g of p-toluenesulfonic acid.

The esterification residue contained 7.4% by weight of butyl acrylate 64.5% by weight of butoxyester I (R=$C_4H_9$)

19.2% by weight of acryloyloxyester II (R=$C_4H_9$)

The cleavage temperature was 195° C. and the operating pressure was 1 atm.

The esterification residue to be cleaved and the corresponding amount of acrylic acid were fed continuously to the cleavage reactor during the cleavage, the level being used for controlling the feed.

The cleavage products were removed in vapor form and condensed at the top of the column (30 cm×2.8 cm, 5 mm Raschig rings) attached to the cleavage reactor.

Per hour, 80 g of esterification residue and 24 g of acrylic acid were fed to the cleavage, and 95 g of distillate were condensed.

According to gas chromatographic analysis, the condensate contained:

71.0% by weight of butyl acrylate 6.5% by weight of butanol 18.5% by weight of acrylic acid 0.4% by weight of dibutyl ether 1.0% by weight of butenes Conversion: 90% by weight, based on the esterification residue.

(B) Hydrolysis of the Cleavage Residue

In a stirred reactor according to Example 1C, a mixture of 524 g of cleavage residue and 780 g of 25% strength sodium hydroxide solution was heated to the boil, and the hydrolysis products were separated off by distillation. The aqueous phase was recycled to the reactor. The temperature in the reactor was initially 97° C. and increased to 103° C. in the course of 4 hours. According to gas chromatographic analysis, the organic phase (208 g) contained in particular butanol (78%) and water (17%).

Altogether, it was accordingly possible to recover about 104 g of butanol and about 843 g of butyl acrylate from 1000 g of bottom product of the esterification.

We claim:

1. A process for the esterification of (meth)acrylic acid with an alkanol in the presence of an esterification catalyst, in which uncoverted starting compounds and the (meth) acrylate to be formed are separated off by distillation and an oxyester-containing bottom product is formed and is separated off, and (a) in the bottom product separated off, the oxyesters present are cleaved, if required after the addition of (meth)acrylic acid and/or oligomeric (meth)acrylic acid, directly in the presence of acid catalysts differing from the (meth)acrylic acid and/or oligomeric (meth) acrylic acid, and the cleavage products are removed, a cleavage residue remaining, or (b) the oxyesters are first removed by distillation from the bottom product separated off, a distillation residue remaining, and the oxyesters removed are cleaved, if required after addition of (meth)acrylic acid and/or oligomeric (meth)acrylic acid, in the presence of acid catalysts differing from (meth)acrylic acid and/or oligomeric (meth)acrylic acid, and the cleavage products are removed, a cleavage residue remaining, wherein the cleavage residue in step (a) or the cleavage residue obtained in step (b) is hydrolytically cleaved together with the resulting distillation residue in the presence of at least 20% by weight of water based on the amount of cleavage residue and any distillation residue, and acids or bases.

2. A process as claimed in claim 1, wherein the cleavage in step (a) or (b) is carried out at from 150 to 250° C. and the hydrolytic cleavage is carried out at from 80 to 120° C.

3. A process as claimed in claim 1, wherein the cleavage products formed in the cleavage of the oxyesters are recycled directly to the esterification.

4. A process as claimed in claim 1, wherein the hydrolysis products formed in the hydrolytic cleavage are distilled off with a part of the water and, after phase separation into an aqueous and an organic phase, the aqueous phase is recycled to the hydrolytic cleavage and the organic phase to the esterification.

5. A process as claimed in claim 1, wherein the acid catalyst used in steps (a) and (b) is a mineral acid or an organic acid differing from (meth)acrylic acid and oligomeric (meth)acrylic acid.

6. A process as claimed in claim 1, wherein the acid used for the hydrolytic cleavage is a mineral acid or an organic acid differing from (meth)acrylic acid and oligomeric (meth) acrylic acid or is an acid present in the cleavage residue, and the base used is an alkali metal hydroxide or alkaline earth metal hydroxide.

7. A process as claimed in claim 1, wherein water in an amount from 20 to 100% by weight, based on the amount of cleavage residue and any distillation residue, is added to the hydrolytic cleavage.

8. A process as claimed in any of claims 1 to 7, wherein the cleavage in steps (a) and (b) is carried out under reduced pressure (<1 atm).

9. A process as claimed in claim 1, wherein the alkanol used is a $C_{1-12}$-alkanol.

10. A process as claimed in claim 1, wherein an oxygen-containing stripping gas is passed through the cleavage residue and any distillation residue in order to remove the cleavage products in steps (a) and (b) or in the hydrolytic cleavage.

11. A process as claimed in claim 1, wherein water is added in an amount from 20 to 200% by weight, based on the amount of cleavage residue and any distillation residue, and acids or bases.

12. A process as claimed in claim 1, wherein water is added in an amount from 50 to 150% by weight, based on the amount of cleavage residue and any distillation residue, and acids or bases.

13. A process as claimed in claim 10, wherein said stripping gas is air.

14. A process as claimed in claim 10, wherein said stripping gas is a mixture of air with an inert gas.

15. A process as claimed in claim 14, wherein said inert gas is nitrogen.

* * * * *